(12) United States Patent
Mika

(10) Patent No.: US 7,195,637 B2
(45) Date of Patent: Mar. 27, 2007

(54) METHOD AND DEVICE FOR INSERTING LEADS INTO CORONARY VEINS

(75) Inventor: Yuval Mika, Yaacov (IL)

(73) Assignee: Impulse Dynamics N.V., Curacao (AN)

( * ) Notice: Subject to any disclaimer, the term of this patent is extended or adjusted under 35 U.S.C. 154(b) by 582 days.

(21) Appl. No.: 10/257,722

(22) PCT Filed: Apr. 17, 2001

(86) PCT No.: PCT/IL01/00348

§ 371 (c)(1),
(2), (4) Date: Dec. 2, 2002

(87) PCT Pub. No.: WO01/78574

PCT Pub. Date: Oct. 25, 2001

(65) Prior Publication Data

US 2004/0010281 A1 Jan. 15, 2004

(51) Int. Cl.
*A61B 17/00* (2006.01)
(52) U.S. Cl. ..................................... 606/190
(58) Field of Classification Search ............... 606/190, 606/192, 108; 604/96.01, 99.01, 103, 103.05, 604/103.11; 623/1.11
See application file for complete search history.

(56) References Cited

U.S. PATENT DOCUMENTS

| | | | |
|---|---|---|---|
| 4,738,666 A | * | 4/1988 | Fuqua ........................ 604/514 |
| 4,928,688 A | | 5/1990 | Mower |
| 6,317,631 B1 | | 11/2001 | Ben-Haim et al. |
| 6,368,337 B1 | * | 4/2002 | Kieturakis et al. .......... 606/190 |

FOREIGN PATENT DOCUMENTS

WO     WO 00/04947     3/2000

* cited by examiner

*Primary Examiner*—Kevin T. Truong
(74) *Attorney, Agent, or Firm*—Wolf, Block, Schorr & Solis-Cohen LLP; William H. Dippert

(57) ABSTRACT

A method for inserting a lead into coronary veins of a patient. The method comprises providing a guide sheath that comprises a tube having a proximal portion and a distal portion; a lumen passing through said tube, said lumen is provided with a first opening in said proximal portion and a second opening in said distal portion, said lumen is adapted to allow the lead to pass through it; a balloon provided in said distal portion, said balloon is adapted to be inflated outwardly and circumferentially from said tube; a tubing fluidically connected to said balloon, said tubing extends from said balloon to said proximal portion. The method further comprises inserting the guide sheath into a coronary vein; inflating said balloon so as to prevent retrograde blood flow from the coronary vein; inserting the lead into the coronary vein through said lumen and placing it in a target location. When the balloon is inflated, retrograde blood flow from the coronary veins is prevented, the pressure in the coronary veins is increased and the coronary veins are enlarged allowing the lead to freely advance through them.

22 Claims, 3 Drawing Sheets

METHOD AND DEVICE FOR INSERTING LEADS INTO CORONARY VEINS

FIELD OF THE INVENTION

The present invention relates to methods for inserting implantable systems. More particularly, the present invention relates to guide sheath that facilitates the insertion of leads into coronary veins.

BACKGROUND OF THE INVENTION

Guide sheaths that facilitate insertion of in vivo devices in general, and electrode leads in particular, are known in the art. Since the insertion and the placement of a lead by itself is complicated due to the flexibility of the device and the contractility of the body lumens, the lead is usually inserted through a stiff guide sheath that is inserted into the body lumen ahead of the lead insertion. The complexity of inserting leads is further enhanced when the lead is inserted into veins due to particular problems that will be comprehensively explained herein after.

Several particular treatment methods in which the insertion of a lead is required, faces additional difficulties. For example, several devices require the delivery of electric signals to the left ventricle of the heart. In PCT/IL97/00012, published as WO 97/25098, titled ELECTRICAL MUSCLE CONTROL (Ben-Haim et al.), a lead is used for the delivery of contractility modulation non-excitatory signals to the left ventricle surface. In PCT/IL99/00392, published as WO 00/04947, titled PACING WITH HEMODYNAMIC ENHANCEMENT (Darvish et al.), one or more electrodes are used for respective cardiac muscle segments pacing with hemodynamic improvement. The placement of the electrode lead is very important in cases such as these, hence the placement of such leads on the surface of the left ventricle is desirable. A method that allows placing the electrode lead on the surface of the left ventricle involves the insertion of the lead to a vein reaching the right atrium and inserting it to the coronary sinus, which is the drain of the coronary veins. Through the coronary veins, it is possible to place the lead on top of the left ventricle surface.

Other methods are available for treating hemodynamic disfunction. An example for such method in which insertion of electrode lead into the coronary veins is advantageous, is biventricular pacing. Examples for the use of biventricular pacing are widely available and in the patent literature, an example is disclosed in U.S. Pat. No. 4,928,688 "METHOD AND APPARATUS FOR TREATING HEMODYNAMIC DISFUCTION" filed in 1989 by Mower, in which hemodynamic disfunction is treated by simultaneously pacing both ventricles of the heart.

Inserting electrode leads into the coronary veins faces several additional difficulties, as follows:
1. Chronic leads are designed so that maximum flexibility is allowed. Flexible electrode lead cannot be forcibly pushed through lumens, especially through veins that are frequently contracted.
2. The coronary veins tend to get narrow towards the apex of the chamber. When there is a need to insert the lead to the vicinity of the apex, the vein itself will impose a considerable resistance to the insertion of the lead. Moreover, the coronary veins become especially tortuous in the vicinity of the coronary sinus so that maneuvering in the veins becomes impossible.
3. The blood in the veins flows towards the coronary sinus so the flow of blood opposite the direction of the lead insertion interferes with the insertion of the lead and pushes the lead itself outwardly.

As the accuracy in the lead placement becomes essential, these problems encountering the lead insertion are intensified.

SUMMARY OF THE INVENTION

It is an object of the present invention to provide a new and unique method for inserting leads into coronary veins through the venous system by which the placement of the lead on the surface of the left ventricle is relatively easy and safe.

Yet, it is another object of the present invention to provide a method for inserting leads into the coronary veins in which the veins are enlarged prior to the insertion of the lead in order to facilitate the insertion of the lead to the narrowest coronary veins. This enables placement of the lead with utmost accuracy.

It is another object of the present invention to provide a new and unique device that facilitates the insertion of leads into the coronary veins.

It is yet another object of the present invention to provide a new and unique guide sheath that is inserted into the coronary vein prior to the insertion of the lead so that to ease and enhance the safety of the lead insertion by enlarging the diameter of the coronary veins prior to the insertion of the lead.

It is thus provided a method for inserting a lead into coronary veins of a patient, said method comprising:
  providing a guide sheath, said guide sheath comprises:
    a tube having a proximal portion and a distal portion;
    a lumen passing through said tube, said lumen is provided with a first opening in said proximal portion and a second opening in said distal portion, said lumen is adapted to allow the lead to pass through it;
    a balloon provided in said distal portion, said balloon is adapted to be inflated outwardly and circumferentially from said tube;
    a tubing fluidically connected to said balloon, said tubing extends from said balloon to said proximal portion;
  inserting said guide sheath into a coronary vein;
  inflating said balloon so as to prevent retrograde blood flow from the coronary vein;
  inserting the lead into the coronary vein through said lumen and placing it in a target location;

whereby when the balloon is inflated, retrograde blood flow from the coronary veins is prevented, the pressure in the coronary veins is increased and the coronary veins are enlarged allowing the lead to freely advance through them.

Furthermore in accordance with another preferred embodiment of the present invention, said method further comprising:
  providing two opposite seams extending from said first opening to said second opening;
  deflating said balloon;
  removing said tube by tearing forcibly said two seams so as to split said tube into two parts.

Furthermore in accordance with another preferred embodiment of the present invention, said guide sheath is removed by a cutting device.

Furthermore in accordance with another preferred embodiment of the present invention, said method further comprising:

providing a second lumen in said tube, parallel to said lumen, said second lumen extends from said proximal portion to said distal portion and has a third opening in said proximal portion and a fourth opening in said distal portion;

inserting fluid to the coronary vein through said second lumen in order to further increase the pressure in the coronary vein.

Furthermore in accordance with another preferred embodiment of the present invention, said method further comprising inserting radio opaque fluid to the coronary veins through said second lumen.

Furthermore in accordance with another preferred embodiment of the present invention, said method further comprising:

providing a pressure sensor electrically communicating with a monitor, said monitor is adapted to show the pressure in the vicinity of the senor;

inserting said pressure sensor into the coronary vein through said second lumen.

Furthermore in accordance with another preferred embodiment of the present invention, said method further comprising providing a unidirectional valve in said second lumen so as to prevent blood from leaking through said third opening.

Furthermore in accordance with another preferred embodiment of the present invention, said method further comprising providing a unidirectional valve in said lumen so as to prevent blood from leaking through said first opening.

Furthermore in accordance with another preferred embodiment of the present invention, said method is further comprising:

threading a second guide sheath through said lumen;

advancing said second guide sheath beyond said guide sheath;

wherein the electrode lead is inserted to the coronary vein through said second lumen.

It is further provided a guide sheath to be inserted into coronary veins in order to facilitate insertion of a lead into a coronary vein, said guide sheath comprises:

a tube having a proximal portion and a distal portion;

a lumen passing through said tube, said lumen is provided with a first opening in said proximal portion and a second opening in said distal portion, said lumen is adapted to allow the lead to pass through it;

a balloon provided in said distal portion, said balloon is adapted to be inflated outwardly and circumferentially from said tube;

a tubing fluidically connected to said balloon, said tubing extends from said balloon to said proximal portion;

whereby after the distal portion of said guide sheath is placed in the coronary vein, the balloon is inflated so as to prevent retrograde flow of blood from the vein and consequently enlarging the vein so that a lead may be freely inserted into the coronary vein.

Furthermore in accordance with another preferred embodiment of the present invention, said tube is provided with two opposite seams, each of said two opposite seams extends from said first opening to said second opening and adapted to be torn upon forcible action and split said tube into two parts.

Furthermore in accordance with another preferred embodiment of the present invention, said proximal portion is provided with two opposite extensions, each extension extends from one of the two splitable parts of said tube, the extensions are adapted to allow grasping the two parts in order to split the tube.

Furthermore in accordance with another preferred embodiment of the present invention, said tube is pre-shaped so as to accord the curves in the venous system directing to the coronary veins.

Furthermore in accordance with another preferred embodiment of the present invention, said tube is made of a material that changes configuration depending on temperature the tube is in.

Furthermore in accordance with another preferred embodiment of the present invention, said tube is made of a biocompatible material.

Furthermore in accordance with another preferred embodiment of the present invention, said tubing is incorporated in said tube.

Furthermore in accordance with another preferred embodiment of the present invention, said tubing slightly extends beyond said proximal portion of said tube and is provided with a lock and an opening through which air may be inserted or withdrawn into and from said balloon using a syringe.

Furthermore in accordance with another preferred embodiment of the present invention, a second lumen is provided in said tube, parallel to said lumen, said second lumen extends from said proximal portion to said distal portion and has a third opening in said proximal portion and a fourth opening in said distal portion.

Finally, in accordance with another preferred embodiment of the present invention, said third opening is provided with a lock and an opening through which fluids may be inserted into said second lumen using a syringe.

DETAILED DESCRIPTION OF THE INVENTION AND THE FIGURES

Some known-cardiac devices (such as ETC devices) require the delivery of electric signals to one of the ventricles of the heart or both of them. A method for inserting such a device involves the placement of the device (an electrode lead) on the surface of the preferred ventricle, for example the left ventricle, by inserting the lead to a vein reaching the right atrium and inserting it into the coronary veins so that the lead is placed on top of the left ventricle surface.

Figure 1:
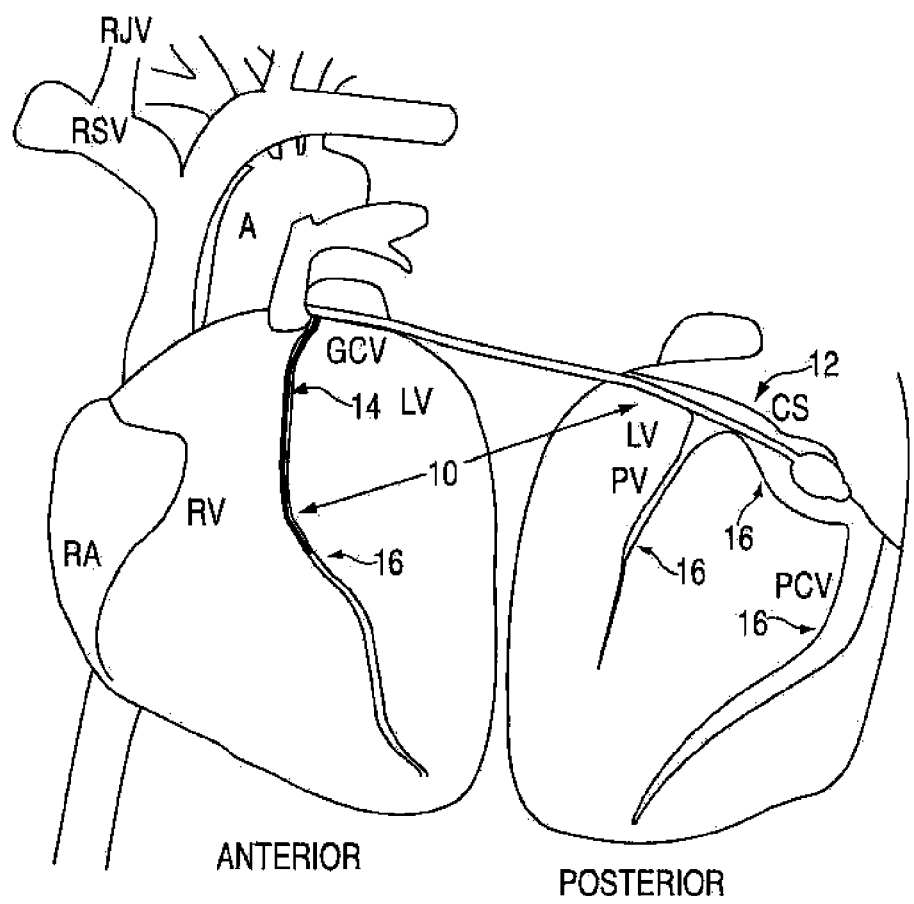
FIG. 1 depicts a heart with posterior and anterior view with a device for inserting leads into the coronary veins in accordance with a preferred embodiment of the present invention.

FIG. 1 depicts a heart with posterior and anterior views with a device for inserting leads into the coronary veins in accordance with a preferred embodiment of the present invention. A lead is to be inserted through the Jugular or Subclavian veins to the right atria. Optionally, a minimal invasive technique to reach the right atria is to directly insert the lead into the atria appendage. From the right atria, the lead is directed into the coronary sinus, goes around the chamber and then turns and descends into the great cardiac vein in the anterior side of the left ventricle. Guide sheath 10 for inserting leads into the coronary veins may be inserted into the position shown in FIG. 1, in the same path as described, into the coronary sinus 12 or the great cardiac vein 14 or further into one of the different veins 16 on the lateral or posterior wall of the left ventricle.

In many cases, the insertion of the guide sheath itself is a difficult task that may be overcome using known methods such as inserting the guide sheath using a guide wire. The guide wire provides the guide sheath with support while advancing through the veins. Another means to facilitate the insertion of the guide sheath is to use of a pre-shaped guide sheath. The insertion of the guide sheath is performed in a predetermined manner so that the path in the veins in which the guide sheath will advance is known. Guide sheath may be designed having curvature that accords the path in which the guide sheath will advance so that to facilitate the insertion of the guide sheath in the desired path. Another means that is available is manufacturing the guide sheath from a material that changes its shape depending of the temperature. In this way, the guide sheath is shaped in a certain shape having certain curvature when the guide sheath is outside the body and during the insertion, while after the guide sheath is in the venous system for a certain time, it will gain other curvature that will facilitate the use of it. Pre-shaped material may be incorporated in the guide sheath of the present invention as one of the components that are contained in the guide sheath or as a independent unit that is inserted through one of the lumens of the guide sheath. An example for a material that may be used in order to pre-shape the guide sheath is nitinol. In any of the cases, the guide sheath of the present invention, including all parts that are intended to be in contact with tissues, is made of a biocompatible material.

Since the coronary veins tend to get narrower towards the apex of the chamber, guide sheath 10 will apparently stop from advancing further into the coronary vein in some point. It is optional to use an additional guide sheath that will be inserted through the guide sheath of the present invention. The narrower guide sheath that is inserted into the venous system in a telescopic manner will be able to advance further into the veins since it is narrower than the outer guide sheath and have the support of the outer guide sheath. The threaded guide sheath gives additional support to the lead that will eventually be inserted into the target vein through the guide sheaths.

The method of the present invention involves the enlargement of the coronary veins in order to facilitate the insertion of the lead into the vein. The muscles in the wall of the veins are relatively compliant and extend as the pressure in the veins increases. The guide sheath of the present invention is designated to block or reduce the flow of blood from the coronary veins to the right atrium so that the pressure in the veins increases and therefore, the diameter of the veins will be increased. When the vein is enlarged, a lead may be easily and accurately inserted and placed in a suitable position in one of the coronary veins. Moreover, the fact that the retrograde flow from the coronary veins partially stops, makes it easier to push the lead inside the vein and against the direction of the flow. In the usual procedure, the lead is pushed against the direction of the blood flow so that the insertion is very difficult. In case the above application in which another guide sheath is threaded through the guide sheath of the present invention is implemented, the thinner guide sheath may be advanced further into the coronary veins after enlarging the veins by the outer guide sheath, using the method that will be discussed herein after.

Figure 2:
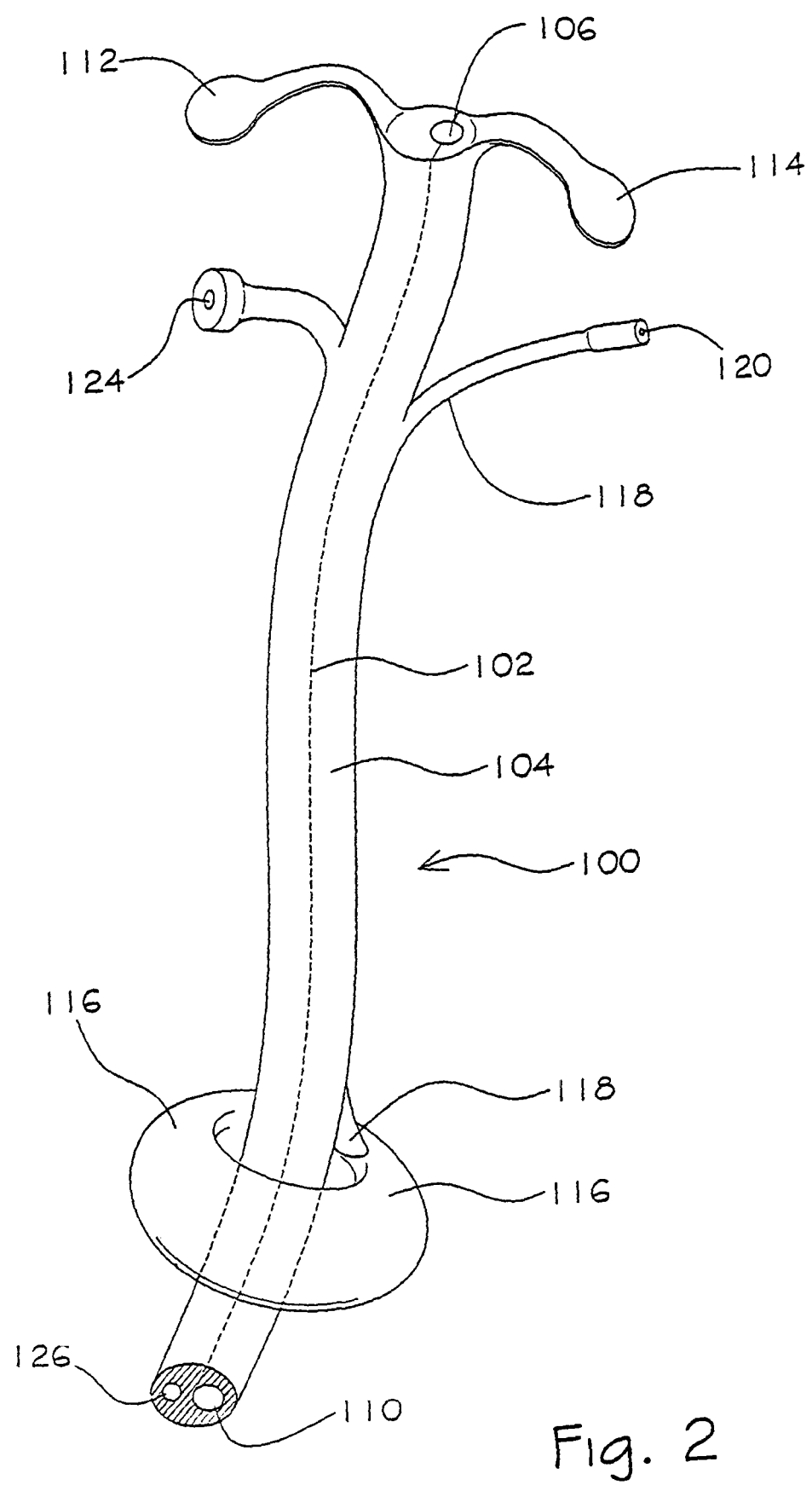
FIG. 2 illustrates an isometric view of a guide sheath for inserting lead into the coronary veins in accordance with a preferred embodiment of the present invention.

Reference is now made to FIG. 2, illustrating an isometric view of a guide sheath for inserting lead into the coronary veins in accordance with a preferred embodiment of the present invention. Guide sheath 100 is preferably a peel-away or splitable guide sheath. A tube 104 that is long enough so it may be inserted and directed towards the heart through the venous system, yet, thin enough so it may be easily inserted into the veins and particularly into an average coronary vein, has a proximal side and a distal side. Tube 104 may be comprised of portions having different stiffness. For example, the tip of the tube in the distal portion may be stiffer than the rest of the tube so that it will be easily maneuvered in the veins. Tube 104 is provided with a lumen 106 through which a standard electrode lead may pass. Lumen 106 has two openings, a first opening 108 is provided in the proximal side of tube 104 and a second opening 110 is provided in the distal side. In order to remove guide sheath 100 from the venous system after the lead is inserted through it and is placed, guide sheath 100 is withdrawn while peeling it from the lead. Two seams 102 are provided along tube 104 in substantially opposite sides so that upon forcible action, tube 104 splits into two elongated parts, each part is substantially half a tube. Two grasping extensions 112 that extend from the tube facilitate the peeling operation. At the tip of both grasping extensions 112, a relatively stiff portion is provided 114. Optionally, the guide sheath of the present invention may be a uniform tube that is cut using a cutting device while discharging the guide sheath after the lead is inserted and anchored.

At the distal side of tube 104, relatively close to the edge of the tube, a balloon 116 is provided. Balloon 116 is made of a relatively soft material so that the balloon may be inflated and deflated, an inflated state is shown in FIG. 2. Similar balloons are used in angioplasty catheters for example, and are well known in the art. Inflation and deflation of balloon 116 is performed through a tubing 118 that extend from the balloon to the proximal side of tube 104. A small portion of tubing 118 extends beyond the proximal portion of the tube and is provided at the end of the extension with a lock and an opening 120 through which air may be inserted or withdrawn using a syringe. After guide sheath 100 is inserted into the coronary vein and properly placed, balloon 116 is inflated causing a blockage or a partial blockage of the veins. Blood is not allowed to return towards the right atrium or the flow of blood is markedly reduced. As explained herein before, such blockage in the returned blood causes an increased pressure in the veins that in turn causes an increase in the diameter of the veins due to compliance characteristics of the veins. When the veins are enlarged, an electrode lead that is inserted through guide sheath 100 from its proximal side may be placed easily and accurately in a proper position using any anchoring means, so that the performance of an electrode exposed on the electrode lead is optimal. The electrode lead may be of any type. After the required placement of the electrode lead is established, balloon 116 is deflated by withdrawing the air through opening 120 and the guide sheath may be retracted by peeling it from the proximal side. The electrode lead is left in spot and may be used in a desirable way.

Optionally, in order to further increase the pressure in the veins, fluid such as saline solution may be pushed to the vein. In order to insert the fluid inside the vein, a second lumen 122 is provided. Lumen 122 extends from the proximal side of tube 104, where a lock and an opening 124 is provided, to the distal side of tube 104, where a second opening 126 is provided. If fluid addition is desired, it may be pushed using a standard syringe through opening 124 and flows through opening 126 into the coronary vein in which the proximal side of guide sheath 100 is positioned. Lumen 122 may also be used for the purpose of injecting radio opaque dye to the coronary veins so that visualization of the coronary veins and a selection of the target vein, into which the lead will be inserted, may be easily performed.

Optionally, lumen 122 may also be used for measuring the pressure inside the coronary veins. Since the procedure of the present invention involves an intentional increase in the pressure inside the coronary veins, it is important that the surgeon will have the ability to control the increased pressure so as to prevent a possible damage to the veins. If the pressure in the coronary veins increase to an undesirable level during the procedure, the surgeon may withdraw some of the air from balloon 116 so as to allow the trapped blood to return to the right atria. After the pressure in the veins goes back to a desirable level, the surgeon may block again the passage of blood by inflating the balloon and continue the procedure.

Figure 3:
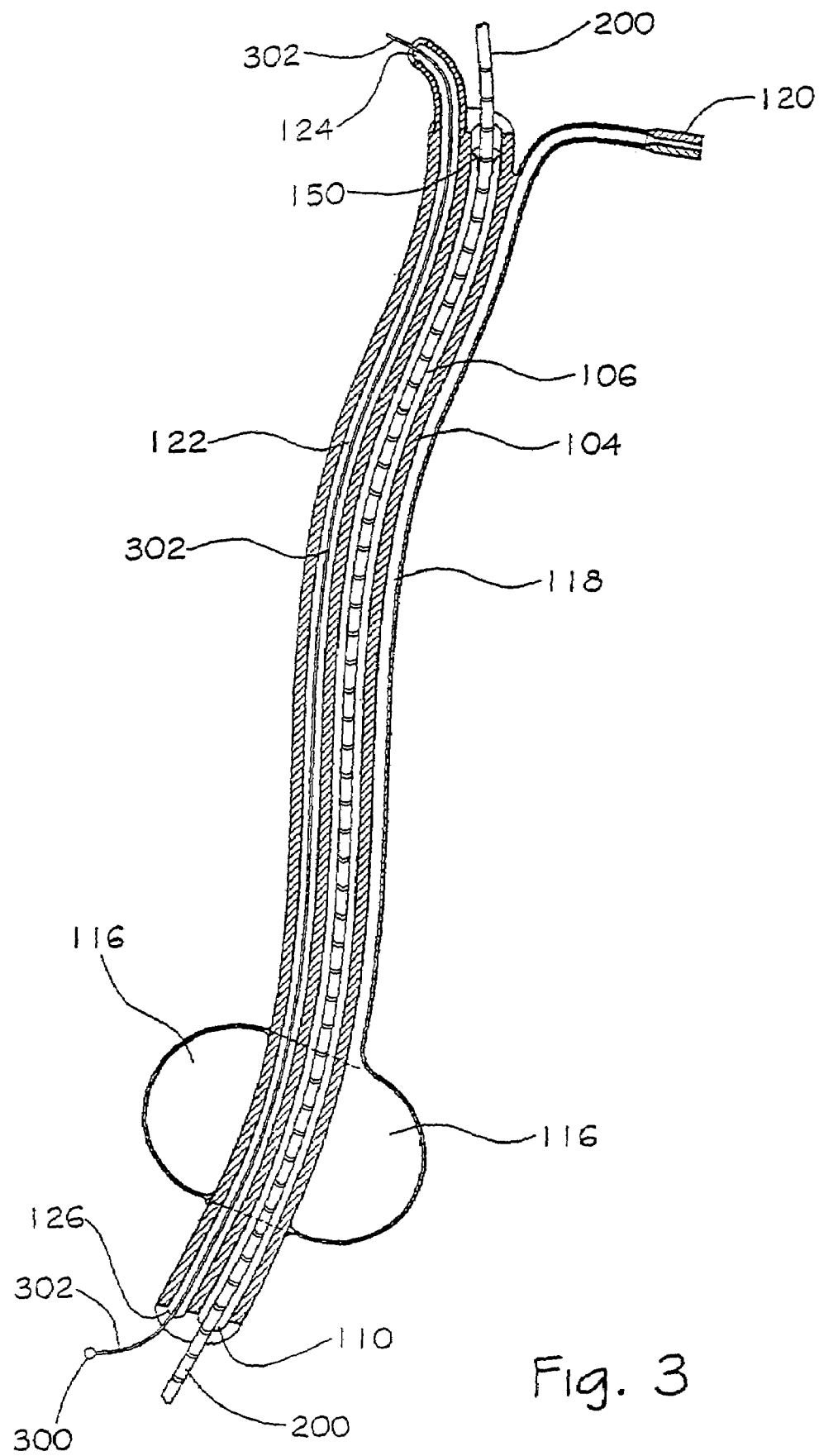
FIG. 3 illustrates a cross sectioned view of the guide sheath shown in FIG. 2 with an electrode lead passing through it.

Reference is now made to FIG. 3, illustrating a cross sectioned view of the guide sheath shown in FIG. 2 with an electrode lead passing through it. Guide sheath 100, as explained herein above, is provided with a lumen, through which an electrode lead 200 may freely pass. Close to opening 108, a unidirectional valve 150 is preferably provided. Unidirectional valve 150 prevents blood from leaking out through opening 108, especially when the pressure in the venous system is increased and the blood is pushed towards the opening. However, unidirectional valve 150 does not interrupt the free insertion of electrode lead through opening 108 into the guide sheath and into the coronary veins. After the placement of the of guide sheath 100 inside one of the coronary veins, balloon 116 is inflated, preventing the retrograde blood from flowing. As a consequence, the coronary vein engorges, allowing the introduction of electrode lead 200 into the portion of the vein that is very narrow in a regular situation. Before or during the insertion of the electrode lead, a pressure sensor may be inserted into the coronary vein through lumen 122. The pressure sensor is used to facilitate the surgeon with information means in order to control the pressure in the vein during the insertion of the lead. Pressure sensor 300 is electrically communicating by wire 302 through an electrical circuitry to a monitor that shows the pressure in the coronary vein (the monitor and the electrical circuitry are standard devices and are not shown in FIG. 3). As explained herein above, the control over the pressure in the coronary vein that is being monitored using pressure sensor 300 is performed by deflating balloon 116, which results in a decrease in the pressure, or inflating it again in order to increase the pressure again.

As explained herein above, the purpose of the method of the present invention is to provide a means that facilitates the insertion of lead into coronary veins having small diameter. The means that facilitates the insertion is the increase in the diameter of the small veins so that an electrode lead may easily be inserted into the vein and be placed. For that reason, the guide sheath of the present Invention is provided with a balloon that may be inflated in order to prevent the retrograde flow of blood and to increase the diameter of the veins or being deflated in order to allow retrograde flow of blood, causing the veins to regain their original diameter.

It should be clear that the description of the embodiments and attached Figures set forth in this specification serves only for a better understanding of the invention, without limiting its scope as covered by the following Claims.

It should also be clear that a person skilled in the art, after reading the present specification could make adjustments or amendments to the attached Figures and above described embodiments that would still be covered by the following Claims.

The invention claimed is:

1. A method for inserting a lead into coronary veins of a patient, said method comprising:
   providing a guide sheath, said guide sheath comprising:
      a tube having a proximal portion and a distal portion;
      a lumen passing through said tube, said lumen being provided with a first opening in said proximal portion and a second opening in said distal portion and said lumen being adapted to allow the lead to pass through it;
      a balloon provided in said distal portion, said balloon being adapted to be inflated outwardly and circumferentially from said tube;
      a tubing in fluid connection with said balloon, said tubing extending from said balloon to said proximal portion;
   inserting said guide sheath into a coronary vein;
   inflating said balloon so as to prevent retrograde blood flow from the coronary vein; and
   inserting the lead into the coronary vein through said lumen and placing it in a target location,
   wherein when the balloon is inflated, retrograde blood flow from the coronary veins is prevented, the pressure in the coronary veins is increased, and the coronary veins are enlarged, allowing the lead to freely advance through them.

2. The method claimed in claim 1, wherein said method further comprises:
   providing two opposite seams extending from said first opening to said second opening;
   deflating said balloon; and
   removing said tube by forcibly tearing said two seams so as to split said tube into two parts.

3. The method as claimed in claim 1, wherein said guide sheath is removed by a cutting device.

4. The method as claimed in claim 1, wherein said method further comprises:
   providing a second lumen in said tube, parallel to said lumen, said second lumen extending from said proximal portion to said distal portion and having a third opening in said proximal portion and a fourth opening in said distal portion; and
   inserting fluid into the coronary vein through said second lumen in order to further increase the pressure in the coronary vein.

5. The method as claimed in claim 4, wherein said method further comprises inserting radio-opaque fluid into the coronary veins through said second lumen.

6. The method as claimed in claim 4, wherein said method further comprises:
   providing a pressure sensor electrically communicating with a monitor, said monitor being adapted to show the pressure in the vicinity of the sensor; and
   inserting said pressure sensor into the coronary vein through said second lumen.

7. The method as claimed in claim 4, wherein said method further comprises providing a unidirectional valve in said second lumen so as to prevent blood from leaking through said third opening.

8. The method as claimed in claim 1, wherein said method further comprises providing a unidirectional valve in said lumen so as to prevent blood from leaking through said first opening.

9. The method as claimed in claim 1, wherein said method further comprises:

threading a second guide sheath through said lumen; and advancing said second guide sheath beyond said guide sheath, wherein the electrode lead is inserted to the coronary vein through said second lumen.

10. A guide sheath to be inserted into coronary veins in order to facilitate insertion of a lead into a coronary vein, said guide sheath comprising:

a tube having a proximal portion and a distal portion;

a lumen passing through said tube, said lumen being provided with a first opening in said proximal portion and a second opening in said distal portion, said lumen being adapted to allow the lead to pass through it;

a balloon provided in said distal portion, said balloon being adapted to be inflated outwardly and circumferentially from said tube;

tubing in fluid connection with said balloon, said tubing extending from said balloon to said proximal portion, wherein after the distal portion of said guide sheath is placed in the coronary vein, the balloon is inflated so as to prevent retrograde flow of blood from the vein and to consequently enlarge the vein so that a lead may be freely inserted into the coronary vein.

11. A guide sheath as claimed in claim 10, wherein said tube is provided with two opposite seams, each of said two opposite seams extending from said first opening to said second opening and being adapted to be torn upon forcible action and split said tube into two parts.

12. A guide sheath as claimed in claim 11, wherein said proximal portion is provided with two opposite extensions, each extension extending from one of the two splitable parts of said tube, and the extensions being adapted to allow grasping of the two parts in order to split the tube.

13. A guide sheath as claimed in claim 10, wherein said tube is pre-shaped so as to accord the curves in the venous system directing to the coronary veins.

14. A guide sheath as claimed in claim 10, wherein said tube is made of a material that changes configuration depending on the temperature surrounding the tube.

15. The guide sheath as claimed in claim 14, wherein said tube is made of a biocompatible material.

16. A guide sheath as claimed in claim 10, wherein said tube is made of a biocompatible material.

17. A guide sheath as claimed in claim 10, wherein said tubing is incorporated in said tube.

18. The guide sheath as claimed in claim 17, wherein said tubing slightly extends beyond said proximal portion of said tube and is provided with a lock and an opening through which air may be inserted or withdrawn into and from said balloon using a syringe.

19. The guide sheath as claimed in claim 10, wherein a second lumen is provided in said tube, parallel to said lumen, and said second lumen extends from said proximal portion to said distal portion and has a third opening in said proximal portion and a fourth opening in said distal portion.

20. The guide sheath as claimed in claim 19, wherein said third opening is provided with a lock and an opening through which fluids may be inserted into said second lumen using a syringe.

21. The guide sheath as claimed in claim 10, wherein said tubing slightly extends beyond said proximal portion of said tube and is provided with a lock and an opening through which air may be inserted or withdrawn into and from said balloon using a syringe.

22. A guide sheath to be inserted into coronary veins in order to facilitate insertion of a lead into a coronary vein, said guide sheath comprising:

a tube having a proximal portion and a distal portion;

a lumen passing through said tube, said lumen being provided with a first opening in said proximal portion and a second opening in said distal portion, said lumen being adapted to allow the lead to pass through it;

a balloon provided in said distal portion, said balloon being adapted to be inflated outwardly and circumferentially from said tube;

tubing in fluid connection with said balloon, said tubing extending from said balloon to said proximal portion, wherein said guide sheath is adapted to be capable of being inserted into a coronary vein and wherein after the distal portion of said guide sheath is placed in the coronary vein, the balloon is inflated so as to prevent retrograde flow of blood from the vein and to consequently enlarge the vein so that a lead may be freely inserted into the coronary vein.

* * * * *